(12) United States Patent
Havenga et al.

(10) Patent No.: US 6,803,234 B2
(45) Date of Patent: Oct. 12, 2004

(54) GENE DELIVERY VECTORS WITH CELL TYPE SPECIFICITY FOR PRIMARY HUMAN CHONDROCYTES

(75) Inventors: Menzo Havenga, Alphen a/d Rijn (NL); Ronald Vogels, Linschoten (NL); Abraham Bout, Moerkapelle (NL)

(73) Assignee: Crucell Holland B.V., Leiden (NL)

( * ) Notice: Subject to any disclaimer, the term of this patent is extended or adjusted under 35 U.S.C. 154(b) by 0 days.

(21) Appl. No.: 09/928,262

(22) Filed: Aug. 10, 2001

(65) Prior Publication Data

US 2002/0115218 A1 Aug. 22, 2002

Related U.S. Application Data

(60) Provisional application No. 60/224,911, filed on Aug. 11, 2000.

(30) Foreign Application Priority Data

Aug. 10, 2000 (EP) .............................................. 00202835

(51) Int. Cl.$^7$ ............................................... C12N 15/86
(52) U.S. Cl. ........................ 435/456; 435/455; 435/371; 424/93.21
(58) Field of Search ........................ 424/93.21; 435/455, 435/456, 371, 320.1, 325, 366; 514/44

(56) References Cited

U.S. PATENT DOCUMENTS

| | | | | |
|---|---|---|---|---|
| 5,846,782 A | * | 12/1998 | Wickham et al. | ............ 435/697 |
| 6,315,992 B1 | * | 11/2001 | Noh et al. | ................ 424/93.21 |
| 6,455,314 B1 | * | 9/2002 | Wickham et al. | ............ 435/456 |

FOREIGN PATENT DOCUMENTS

| | | |
|---|---|---|
| WO | WO 00/03029 | 1/2000 |
| WO | WO 00/52186 | 9/2000 |

OTHER PUBLICATIONS

Verma, Nature, vol. 389, pp. 239–242, 1997.*
Anderson et al., Nature, vol. 392, pp. 25–30, 1998.*
Doherty et al. (Osteoarthritis and Cartilage, vol. 6, pp. 153–160, 1998.*
Ikeda et al., The Journal of Rheumatology, vol. 27, pp. 990–996, 2000.*

Nixon et al. Clinical Orthopaedics and Related Research, vol. 379S, pp. S201–213, 2000.*

Arai et al., Adenovirus Vector–Mediated Gene Transduction to Chondrocytes: In Vitro Evaluation of Therapeutic Efficacy of Transforming Growth Factor–beta1 and Heat Shock Protein 70 Gene Transduction, Journal of Rheumatology, 1997, pp. 1787–1795, vol. 24, No. 9.

Arai et al., Control of Delivered Gene Expression in Chondrocytes Using Heat Shock Protein 70B Promoter, Journal of Rheumatology, Aug. 1999, pp. 1769–1774, vol. 26, No. 8.

Baragi et al., Transplantation of Transduced Chondrocytes Protects Articular Cartilage from Interleukin 1–Induced Extracellular Matrix Degradation, Journal of Clinical Investigation, 1995, pp. 2454–2460, vol. 96, No. 5.

Duprez et al., Overexpression of BMP–2 and BMP–4 alters the size and shape of developing skeletal elements in the chick limb, Mechanisms of Development, 1996, pp. 145–157, vol. 57, No. 2.

Smith et al., Genetic Enhancement of Matrix Synthesis By Articular Chondrocytes, Arthritis and Rheumatism, May 2000, pp. 1156–1164, vol. 43, No. 5.

* cited by examiner

*Primary Examiner*—Scott D. Priebe
*Assistant Examiner*—Brian Whiteman
(74) *Attorney, Agent, or Firm*—Traskbritt

(57) ABSTRACT

The present invention relates to a gene delivery vehicle comprising a recombinant adenovirus having a tropism for a primary human chondrocyte. By efficiently transducing a nucleic acid of interest into a primary chondrocytes, the gene delivery vehicle is able to at least in part improve the counteraction of cartilage disease. In one embodiment the recombinant adenovirus comprises a deletion in the gene encoding for fiber protein, which is replaced by a nucleic acid sequence encoding at least part of a fiber protein of a B-type adenovirus.

10 Claims, 4 Drawing Sheets

GENE DELIVERY VECTORS WITH CELL TYPE SPECIFICITY FOR PRIMARY HUMAN CHONDROCYTES

CROSS REFERENCE TO RELATED APPLICATIONS

This patent application claims priority from U.S. Provisional Patent Application No. 60/224,911 filed on Aug. 11, 2000.

FIELD OF THE INVENTION

The invention relates to the field of molecular genetics and medicine. In particular the present invention relates to the field of gene therapy, more in particular to gene therapy using adenoviruses.

BACKGROUND OF THE INVENTION

At present in gene therapy, genetic information is delivered to a host cell in order to either correct (supplement) a genetic deficiency in the cell, or to inhibit an unwanted function in the cell, or to eliminate the host cell. Of course the genetic information can also be intended to provide the host cell with a wanted function, for instance to supply a secreted protein to treat other cells of the host, etc. Thus there are at least three different approaches in gene therapy, one directed towards compensating a deficiency present in a (mammalian) host; the second directed towards the removal or elimination of unwanted substances (organisms or cells); and the third towards providing a cell with a wanted function.

For the purpose of gene therapy, adenoviruses have been proposed as suitable vehicles to deliver genes to the host. Gene-transfer vectors derived from adenoviruses (so-called adenoviral vectors) have a number of features that make them particularly useful for gene transfer. 1) The biology of the adenoviruses is characterized in detail, 2) the adenovirus is not associated with severe human pathology, 3) the virus is extremely efficient in introducing its DNA into the host cell, 4) the virus can infect a wide variety of c ells and has a broad host-range, 5) the virus can be produced at high virus titers in large quantities, and 6) the virus can be rendered replication defective by deletion of the early-region 1 (E1) of the viral genome (Brady and Crystal 1994).

However, there are still drawbacks associated with the use of adenoviral vectors especially the well investigated serotypes of subgroup C adenoviruses. These serotypes require the presence of the Coxsackie adenovirus receptor (CAR) on cells for successful infection. Although this protein is expressed by many cells and established cell lines, this protein is absent on many other primary cells and cell lines making the latter cells difficult to infect with serotypes 1, 2, 5, and 6.

The adenovirus genome is a linear double-stranded DNA molecule of approximately 36000 base pairs. The adenovirus DNA contains identical Inverted Terminal Repeats (ITR) of approximately 90–140 base pairs with the exact length depending on the serotype. The viral origins of replication are within the ITRs exactly at the genome ends. Most adenoviral vectors currently used in gene therapy have a deletion in the E1 region, where novel genetic information can be introduced. The E1 deletion renders the recombinant virus replication defective. It has been demonstrated extensively that recombinant adenovirus, in particular serotype 5 is suitable for efficient transfer of genes in vivo to the liver, the airway epithelium and solid tumors in animal models and human xenografts in immunodeficient mice (Bout 1996; Blaese et al. 1995). At present, six different subgroups of human adenoviruses have been proposed which in total encompasses 51 distinct adenovirus serotypes. Besides these human adenoviruses an extensive number of animal adenoviruses have been identified (Ishibashi and Yasue 1984).

A serotype is defined on the basis of its immunological distinctiveness as determined by quantitative neutralization with animal antisera (horse, rabbit). If neutralization shows a certain degree of cross-reaction between two viruses, distinctiveness of serotype is assumed if A) the hemagglutinins are unrelated, as shown by lack of cross-reaction on hemagglutination-inhibition, or B) substantial biophysical/biochemical differences in DNA exist (Francki et al. 1991). The nine serotypes identified last (42–51) were isolated for the first time from HIV-infected patients (Hierholzer et al. 1988; Schnurr and Dondero 1993; De Jong et al. 1999). For reasons not well understood, most of such immunocompromised patients shed adenoviruses that were rarely or never isolated from immuno-competent individuals (Hierholzer et al. 1988; Hierholzer 1992; Khoo et al. 1995, De Jong et al. 1999).

At present the adenovirus serotype 5 is most widely used for gene therapy purposes. Similar to serotypes 2, 4 and 7, serotype 5 has a natural affiliation towards lung epithelia and other respiratory tissues. In contrast, it is known that, for instance, serotypes 40 and 41 have a natural affiliation towards the gastrointestinal tract. For a detailed overview of the disease association of the different adenovirus serotype see Table I. In this Table I there is one deviation from the literature. Sequence analysis and hemagglutination assays using erythrocytes from different species performed in our institute indicated that in contrast to the literature (De Jong et al. 1999) adenovirus 50 proved to be a D group vector whereas adenovirus 51 proved to be a B-group vector.

The natural affiliation of a given serotype towards a specific organ can either be due to a difference in the route of infection i.e., make use of different receptor molecules or internalization pathways. However, it can also be due to the fact that a serotype can infect many tissues/organs but it can only replicate in one organ because of the requirement of certain cellular factors for replication and hence clinical disease. At present it is unknown which of the above mentioned mechanisms is responsible for the observed differences in human disease association. However it is known that different adenovirus serotypes can bind to different receptors due to sequence dissimilarity of the capsid proteins, e.g. fiber proteins. For instance, it has been shown that adenoviruses of subgroup C such as Ad2, and Ad5 bind to different receptors as compared to adenoviruses from subgroup B such as Ad3 (Defer et al. 1990). An adenovirus from subgroup B is referred to as a B-type adenovirus. Likewise, it was demonstrated that receptor specificity could be altered by exchanging the Ad3 with the Ad 5 knob protein, and vice versa (Krasnykh et al. 1996; Stevenson et al. 1995 and 1997). The C-terminus of the fiber protein, or knob, is responsible for initial interaction with the cellular adenovirus receptor. Thus the fiber protein is mainly responsible for receptor specificity. As different host cells can have different receptors, the fiber protein largely determines at which host cells the adenovirus preferably binds. The preference for binding to a certain kind of host cell is called a tropism. If an adenovirus has a tropism for a certain host cell, it may, or may not, bind to other kind of cells as well. The tropism of an adenovirus is thus at least partly dependent on the kind of fiber protein, and/or knob protein.

In the United States alone 95,000 knee replacements and 41,000 other surgical procedures to repair cartilaginous defects of the knee are performed on an annual basis. This, together with other cartilage diseases (i.e. joint surface irregularities, craniofacial deformation, osteogenesis imperfecta, meniscal injury, anencephaly, intra articular fractures, osteoporosis, osteoarthritis, spinal cord fusion, and rheumatoid arthritis) warrant the enormous interest in understanding the underlying biological and biochemical defects of the diseases as well as the interest in gene therapy as a possible cure (reviewed in Frenkel and DiCesare 1999). The strategies to treat these diseases are diverse ranging from direct delivery of genes to sites of injuries, to cell-based delivery approaches, or ex vivo tissue engineering. In case genes are directly delivered to a site of injury either retroviruses, adenoviruses, naked DNA, or liposome complexed DNA are contemplated (Madry and Trippel 2000; Lubberts et al. 1999; Goto et al 1999). The DNA can encode either for amino acid sequences that inhibit the disease progression and/or amino acid sequences that counteract the loss of cartilage. Non-limiting examples of genes that inhibit disease progression are TGFbeta (Nishida et al. 1999), IL-4 (Lubberts et al. 1999), p16INK4a (Taniguchi et al. 1999), IL-I (Fernandez et al. 1999), IL-10 (Whalen et al. 1999), or substances (anti-inflammatory drugs, TNFa, immunosuppressive agents) which can down regulate the activity of NOS or COX (Amin et al. 1999). Both other strategies, cell based or ex vivo bioengineering, use the same genes (Gazit et al. 1999): two pleiotropic inflammatory mediators overproduced in arthritis infected joints. Non-limiting examples of genes that counteract the cartilage degradation are the family of bone morphogenesis proteins (Mason et al. 1998; Kramer et al 2000, Pizette and Niswander 2000). Cells of choice to perform cell based delivery at sites of injury or transplanted into a scaffold are chondrocytes or mesenchymal stem cells derived from human bone marrow (Richardson et al. 1999, Silverman et al. 2000, Gazit et al. 1999). For all these strategies to become therapeutically interesting the delivery of gene sequences chondrocytes needs to be very efficient such that a) expression levels of the therapeutic genes are high and b) low dosages of the gene transfer vehicle, i.e. adenoviruses can be applied to circumvent possible vector-mediated toxic effects.

DETAILED DESCRIPTION

Figure 1:
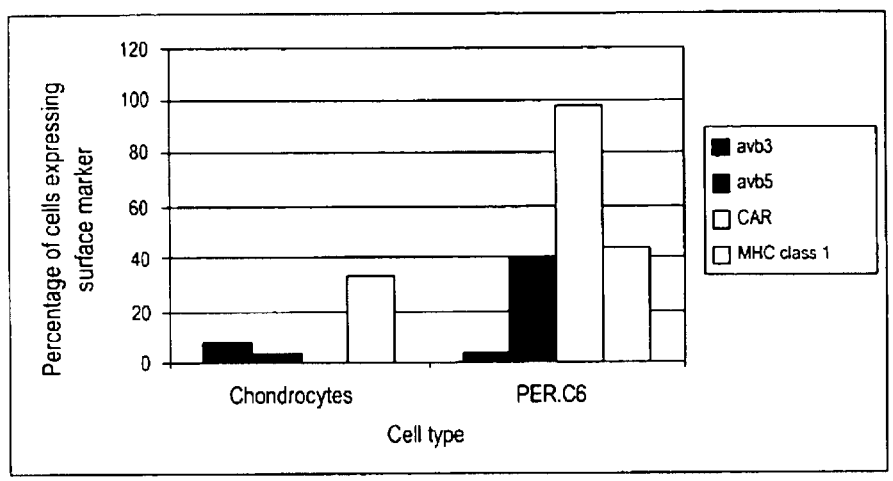
FIG. 1: Expression of CAR, MHC-class I, and $a_v$-integrins on primary chondrocytes. As a control for the antibodies PER.C6 cells were taken along.

The present invention solves the problem of how cartilage diseases can be counteracted by efficiently transducing a nucleic acid into primary chondrocytes. For that purpose, a gene delivery vehicle comprising a recombinant adenovirus having a tropism for primary human chondrocytes has been constructed. By a gene delivery vehicle is meant a carrier which can deliver at least one nucleic acid to a host cell. The nucleic acid that is delivered to a host cell may comprise a nucleic acid sequence encoding an amino acid sequence. The nucleic acid may further comprise at least one promoter, and/or enhancer, and/or terminator. It may also comprise transcription initiation sites, and the like. By delivering a nucleic acid to a host cell, the nucleic acid is moved from the outside to the inside of the host cell. Transient expression of the transgene is sufficient to trigger cells to form bone, or trigger angiogenesis. Therefore a non-integrating vector is preferred i.e. adenovirus. The present invention shows that primary human chondrocytes do not express detectable levels of CAR or MHC-class I, as is described in example 4. The latter indicates that it is difficult to transduce primary human chondrocytes with an adenovirus that enters the cells via these molecules, as for example the commonly-used adenovirus serotype 5. One may use very high titers of the adenovirus, but this, has several disadvantages such as a strong immune response caused by de novo synthesis of adenoviral genes that can subsequently by loaded in MHC class I complexes and presented to the immune system once the cells are transplanted in a host. To avoid toxic side effects, one would like to be able to transfer a nucleic acid to primary human chondrocytes by a gene delivery vehicle with high efficacy. High efficiency of infection allows for a reduction in the viral load that results in less virus binding to cells other than the target cells of interest. If the gene delivery vehicle infects too many other cells, the expression of the delivered nucleic acid in those other cells may cause many side effects. Therefore, the present invention discloses a gene delivery vehicle which has been made specific for a primary chondrocyte and which has the other properties of adenoviruses, for example not integrating its DNA in the host cell genome. To provide specificity for chondrocytes, the present invention discloses an adenovirus that comprises a deletion in the gene encoding for fiber protein that is replaced by a nucleic acid sequence encoding an amino acid sequence having a tropism for primary human chondrocytes. The nucleic acid sequence encoding an amino acid sequence having a tropism for primary human chondrocytes may be derived from any gene encoding for fiber protein. It may comprise at least one mutation that makes it different from any wild type gene encoding for fiber protein. Otherwise, the nucleic acid may be an unmodified gene encoding for fiber protein of any serotype. If the adenovirus disclosed in this invention comprises nucleic acid sequences of at least two different serotypes, the adenovirus is referred to as a chimeric adenovirus.

Although primary human chondrocytes do not express detectable levels of CAR protein, the adenovirus disclosed in the present invention is well capable of infecting the chondrocytes. Therefore it is possible to use a recombinant, adenovirus that is derived from an adenovirus serotype 5 sequence, although an adenovirus serotype 5 normally does not infect primary chondrocytes. The recombinant adenovirus may comprise an adenovirus 5 nucleic acid sequence. It may comprise an adenovirus 5 genome, comprising at least one deletion in its E1 region where a nucleic acid of interest is inserted or can be inserted.

In the counteraction of cartilage diseases, the nucleic acid which is delivered to primary human chondrocytes preferably either encodes an amino acid sequence that inhibits cartilage disease progression or a amino acid sequence that counteracts the loss of cartilage. The nucleic acid can encode a member of the family of bone morphogenesis proteins. Alternatively, the nucleic acid can encode an amino acid sequence which provides the host cell with another wanted function.

Another feature of the present invention is the means to produce a chimeric virus. Typically, one does not want an adenovirus batch to be administered to a host cell that contains replication competent adenovirus, although this is not always true. In general therefore it is desired to omit a number of genes (but at least one) from the adenoviral genome on the vector encoding the chimeric virus and to supply these genes in the genome of the cell in which the vector is brought to produce chimeric adenovirus. Such a cell is usually called a packaging cell. The invention thus also provides a packaging cell for producing a chimeric adenovirus according to the invention, comprising in trans all elements necessary for adenovirus production not present on the adenoviral vector according to the invention. Typically vector and packaging cell have to be adapted to one another in that they have all the necessary elements, but that they do not have overlapping elements which lead to replication competent virus by recombination.

The initial step for successful infection is binding of adenovirus to its target cell, a process mediated through fiber protein. The fiber protein has a trimeric structure (Stouten et al. 1992) with different lengths depending on the virus serotype (Signas et al. 1985; Kidd et al. 1993). Different serotypes have polypeptides with structurally similar N and C termini, but different middle stem regions. N-terminally, the first 30 amino acids are involved in anchoring of the fiber to the penton base (Chrobcczek et al. 1995), especially the conserved FNPVYP (SEQ ID NO:14) region in the tail (Amberg et al. 1997). The knob is responsible for initial interaction with the cellular adenovirus receptor. After this initial binding secondary binding between the capsid penton base and cell-surface integrins is proposed to lead to internalization of viral particles in coated pits and endocytosis (Morgan et al. 1969; Svensson and Persson 1984; Varga et al. 1991; Greber et al. 1993; Wickham et al, 1993).

Integrins are αβ-heterodimers of which at least 14 α-subunits and 8 β-subunits have been identified (Hynes 1992). The array of integrins expressed in cells is complex and will vary between cell types and cellular environment. Although the knob contains some conserved regions, between serotypes, knob proteins show a high degree of variability, indicating that different adenovirus receptors might exist. For instance, it has been demonstrated that adenoviruses of subgroup C (Ad2, Ad5) and adenoviruses of subgroup B (Ad3) bind to different receptors (Defer et al. 1990). By using baculovirus produced soluble CAR as well as adenovirus serotype 5 knob protein, Roelvink et al. (1998) concluded via interference studies that all adenovirus serotypes, except serotypes of subgroup B, enter cells via CAR. The latter, if valid, limits the complexity of using different serotypes for gene therapy purposes.

Besides the involvement in cell binding, the fiber protein also contains the type specific γ-antigen, which together with the ε-antigen of the hexon determines the serotype specificity. The γ-antigen is localized on the fiber and it is known that it consists of 17 amino acids. The anti-fiber antibodies of the host are therefore directed to the trimeric structure of the knob.

It is an object of the present invention to provide a method and means by which an adenovirus can infect primary human chondrocytes. Therefore, the generation of preferably chimeric adenoviruses based for example on adenovirus serotype 5 with modified fiber genes, is described. For this purpose, two or three plasmids, which together contain the complete adenovirus serotype 5 genome, were constructed. From this plasmid the DNA encoding the adenovirus serotype 5 fiber protein was removed and replaced by linker DNA sequences which facilitate easy cloning. The plasmid in which the native adenovirus serotype 5 fiber sequence was partially removed subsequently served as a template for the insertion of DNA encoding for fiber protein derived from different adenovirus serotypes (human or animal). The DNAs derived from the different serotypes were obtained using the polymerase chain reaction technique in combination with (degenerate) oligo-nucleotides. At the former E1 location in the genome of adenovirus serotype 5, any nucleic acid of interest can be cloned. A single transfection procedure of the two or three plasmids together resulted in the formation of a recombinant chimeric adenovirus. Although successful introduction of changes in the adenovirus serotype 5 fiber and penton-base have been reported by others, the complex structure of knob and the limited knowledge of the precise amino acids interacting with CAR render such targeting approaches laborious and difficult.

To overcome the limitations described above we preferred to use pre-existing adenovirus fibers to maximize the chance of obtaining recombinant adenovirus which can normally assemble in the nucleus of a producer cell and which can be produced on pre-existing packaging cells. By generating for example a chimeric adenovirus serotype 5 based fiber library containing fiber proteins of all other human adenovirus serotypes, we have developed a technology which enables rapid screening for a recombinant adenoviral vector with preferred infection characteristics for primary human chondrocytes.

In another aspect the invention describes the construction and use of plasmids consisting of distinct parts of for example adenovirus serotype 5 in which the gene encoding for fiber protein has been replaced with DNA derived from alternative human or animal serotypes. This set of constructs, in total encompassing the complete adenovirus genome, allows for the construction of unique chimeric adenoviruses customized for transduction of particular cell types or organ(s). Also, in this part of the invention means and methods to propagate, produce, and purify fiber chimeric adenoviruses is described.

In another aspect of the invention chimeric viruses are described which have preferred infection characteristics in human primary chondrocytes. The adenoviral vectors preferably are derived from subgroup B adenoviruses or contain at least a functional part of the fiber protein from an adenovirus from subgroup B comprising at least the binding moiety of the fiber protein. In a further preferred embodiment the adenoviral vectors are chimeric vectors based on adenovirus serotype 5 and contain at least a functional part of the fiber protein from adenovirus type 16, 35, or 51. Although adenovirus serotype 5 does not bind to primary chondrocytes, the binding moiety of an adenoviral fiber protein of a B-type adenovirus appears to be sufficient to make the chimeric adenovirus efficiently infect primary chondrocytes. It is to be understood that in all embodiments the adenoviral vectors may be derived from the serotype having the desired properties or that the adenoviral vector is based on an adenovirus from one serotype and contains the sequences comprising the desired functions of another serotype, these sequences replacing the native sequences in the first serotype.

In another aspect of the invention the recombinant adenoviruses may, or may not, contain deletions in the E1 region where a nucleic acid of interest is inserted or can be inserted. Furthermore, chimeric adenoviruses may, or may not, contain deletions in the E3, E2 and/or E4 region where a nucleic acid of interest is inserted or can be inserted. If the nucleic acid of interest does not comprise a promoter, it should be linked to a promoter if the nucleic acid of interest is inserted in the E3, E2 and/or E4 region. If the recombinant adenovirus comprises deletions in the E2 and/or E4 region, E2 and/or E4 complementing cell lines are required to generate recombinant adenoviruses.

Another object of the present invention is a gene delivery vehicle having a tropism for primary human chondrocytes comprising a recombinant adenovirus. This recombinant adenovirus may be a chimeric adenovirus. The recombinant adenovirus may contain a deletion in the gene encoding for fiber protein that is replaced by a nucleic acid encoding an amino acid sequence having a tropism for primary human chondrocytes. As is described in this application, the tropism may be provided by at least a tropism determining part of an adenoviral fiber protein of a B-type adenovirus, and the fiber protein may be derived from an adenovirus type 16, 35 and/or 51. The recombinant adenovirus may comprise an adenovirus 5 nucleic acid sequence and it may comprise an adenovirus 5 genome which at least has a deletion in its E1 region where a nucleic acid of interest is inserted or can be inserted. And it may comprise deletions in its E3, E2 and/or E4 region, where a nucleic acid of interest is inserted or can be inserted, as is described in this application. This recombinant adenovirus may comprise a nucleic acid sequence encoding at least one amino acid sequence that inhibits cartilage disease progression and/or at least one amino acid sequence that counteracts the loss of cartilage.

It may comprise a nucleic acid that encodes at least one member of the family of bone morphogenesis proteins. Also, the nucleic acid may provide the host cell with another wanted function.

Another object of the present invention is a pharmaceutical composition for use in treatment of cartilage diseases. This pharmaceutical composition comprises a gene delivery vehicle as described in the preceding paragraph. The advantage of this pharmaceutical composition is, that it can counteract cartilage diseases in a very efficient way, because it comprises a gene delivery vehicle that infects chondrocytes very efficiently. Because of this efficiency, a small amount will be sufficient. Therefore there will be barely side effects. The immune response will be low. Besides, the pharmaceutical composition comprises a non-integrating vector, which is to be preferred to avoid genome transformation of the host cell and its offspring. Because this pharmaceutical composition comprises a well-known non-integrating vector, it is possible to produce this composition, with the learning of this invention, on a large scale.

EXAMPLES

The examples below are meant to illustrate the present invention. The generation of adenovirus serotype 5 genomic plasmid clones and adenovirus serotype 5 based viruses with chimeric fiber proteins are described. Then primary chondrocytes are tested for expression of integrins and CAR protein. Finally, transduction of human primary chondrocytes with recombinant fiber chimeric adenoviruses is determined. They are not limiting the present invention. A person skilled in the art can perform alternative experiments that are still in the scope of the present invention.

Example 1. Generation of Adenovirus Serotype 5 Genomic 15 Plasmid Clones

The complete genome of adenovirus serotype 5 has been cloned into various plasmids or cosmids to allow easy modification of parts of the adenovirus serotype 5 genome, still retaining the capability to produce recombinant virus. For this purpose the following plasmids were generated:

1. pBr/Ad.Bam-rITR (ECACC deposit P97082122)

In order to facilitate blunt end cloning of the ITR sequences, wild-type human adenovirus type 5 (Ad5) DNA was treated with Klenow enzyme in the presence of excess dNTPs. After inactivation of the Klenow enzyme and purification by phenol/chloroform extraction followed by ethanol precipitation, the DNA was digested with BamHI. This DNA preparation was used without further purification in a ligation reaction with pBr322 derived vector DNA prepared as follows: pBr322 DNA was digested with EcoRV and BamHI, dephosphorylated by treatment with TSAP enzyme (Life Technologies) and purified on LMP agarose gel (SeaPlaque GTG). After transformation into competent *E. coli* DH5α (Life Techn.) and analysis of ampiciline resistant colonies, one clone was selected that showed a digestion pattern as expected for an insert extending from the BamHI site in Ad5 to the right ITR. Sequence analysis of the cloning border at the right ITR revealed that the most 3' G residue of the ITR was missing, the remainder of the ITR was found to be correct. The missing G residue is complemented by the other ITR during replication.

2. pBr/Ad.Sal-rITR (ECACC deposit P97082119)

pBr/Ad.Bam-rITR was digested with BamHI and SalI. The vector fragment including the adenovirus insert was isolated in LMP agarose (SeaPlaque GTG) and ligated to a 4.8 kb SalI-BamHI fragment obtained from wt Ad5 DNA and purified with the Geneclean II kit (Bio 101, Inc). One clone was chosen and the integrity of the Ad5 sequences was determined by restriction enzyme analysis. Clone pBr/Ad.Sal-rITR contains adeno type 5 sequences from the SalI site at bp 16746 up to and including the rITR (missing the most 3' G residue).

3. pBr/Ad.Cla-Bam (ECACC deposit P97082117)

Wild type Adenovirus type 5 DNA was digested with ClaI and BamHI, and the 20.6 kb fragment was isolated from gel by electro-elution. pBr322 was digested with the same enzymes and purified from agarose gel by Geneclean. Both fragments were ligated and transformed into competent DH5α. The resulting clone pBr/Ad.Cla-Bam was analyzed by restriction enzyme digestion and shown to contain an insert with adenovirus sequences from bp 919 to 21566.

4. pBr/Ad.AflII-Bam (ECACC deposit P97082114)

Clone pBr/Ad.Cla-Bam was linearized with EcoRI (in pBr322) and partially digested with AflII. After heat inactivation of AflII for 20' at 65° C. the fragment ends were filled in with Klenow enzyme. The DNA was then ligated to a blunt double stranded oligo linker containing a PacI site (5-AATTGTCTTAATTAACCGCTTAA-3' (SEQ. ID NO. 1)). This linker was made by annealing the following two oligonucleotides: 5'-AATTGTCTTAATTAACCGC-3' (SEQ. ID NO. 2) and 5'-AATTGCGGTTAATTAAGAC-3' (SEQ. ID NO. 3), followed by blunting with Klenow enzyme. After precipitation of the ligated DNA to change buffer, the ligatioris were digested with an excess PacI enzyme to remove concatameres of the oligo. The 22016 bp partial fragment containing Ad5 sequences from bp 3534 up to 21566 and the vector sequences, was isolated in LMP agarose (SeaPlaque GTG), religated and transformed into competent DH5α. One clone that was found to contain the PacI site and that had retained the large adeno fragment was selected and sequenced at the 5' end to verify correct insertion of the PacI linker in the (lost) AflII site.

5. pBr/Ad.Bam-rITRpac#2 (ECACC deposit P97082120) and pBr/Ad.Bam-rITR#8 (ECACC deposit P97082121)

To allow insertion of a PacI site near the ITR of Ad5 in clone pBr/Ad.Bam-rITR about 190 nucleotides were removed between the ClaI site in the pBr322 backbone and the start of the ITR sequences. This was done as follows: pBr/Ad.Bam-rITR was digested with ClaI and treated with nuclease Bal31 for varying lengths of time (2', 5', 10' and 15'). The extent of nucleotide removal was followed by separate reactions on pBr322 DNA (also digested at the ClaI site), using identical buffers and conditions. Ba131 enzyme was inactivated by incubation at 75° C. for 10 min, the DNA was precipitated and resuspended in a smaller volume of TE buffer. To ensure blunt ends, DNAs were further treated with T4 DNA polymerase in the presence of excess dNTPs. After digestion of the (control) pBr322 DNA with SalI, satisfactory degradation (~150 bp) was observed in the samples treated for 10 min or 15 min. The 10 min or 15 min treated pBr/Ad.Bam-rITR samples were then ligated to the above described blunted PacI linkers (See pBr/Ad.AflII-Bam). Ligations were purified by precipitation, digested with excess PacI and separated from the linkers on an LMP agarose gel. After religation, DNAs were transformed into competent DH5α and colonies analyzed. Ten clones were selected that showed a deletion of approximately the desired length and these were further analyzed by T-track sequencing (T7 sequencing kit, Pharmacia Biotech). Two clones were found with the PacI linker inserted just downstream of the rITR. After digestion with PacI, clone #2 has 28 bp and clone #8 has 27 bp attached to the ITR.

pWE/Ad.AflII-rITR (ECACC deposit P97082116)

Cosmid vector pWE15 (Clontech) was used to clone larger Ad5 inserts. First, a linker containing a unique PacI site was inserted in the EcoRI sites of pWE15 creating pWE.pac. To this end, the double stranded PacI oligo as described for pBr/Ad.AflII-BamHI was used but now with its EcoRI protruding ends. The following fragments were then isolated by electro-elution from agarose gel: pWE.pac digested with PacI, pBr/AflII-Bam digested with PacI and BamHI and pBr/Ad.Bam-rITR#2 digested with BamHI and PacI. These fragments were ligated together and packaged using 1 phage packaging extracts (Stratagene) according to the manufacturer's protocol. After infection into host bacteria, colonies were grown on plates and analyzed for presence of the complete insert. pWE/Ad.AflII-rITR contains all adenovirus type 5 sequences from bp 3534 (AflII site) up to and including the right ITR (missing the most 3' G residue).

pBr/Ad.1ITR-Sal (9.4) (ECACC deposit P97082115)

Adenovirus 5 wt DNA was treated with Klenow enzyme in the presence of excess dNTPs and subsequently digested with SalI. Two of the resulting fragments, designated left ITR- Sal (9.4) and Sal (16.7)-right ITR, respectively, were isolated in LMP agarose (Seaplaque GTG), pBr322 DNA was digested with EcoRV and SalI and treated with phosphatase (Life Technologies). The vector fragment was isolated using the Geneclean method (BIO 101, Inc) and ligated to the Ad5 SalI fragments. Only the ligation with the 9.4 kb fragment gave colonies with an insert. After analysis and sequencing of the cloning border a clone was chosen that contained the full ITR sequence and extended to the SalI site at bp 9462.

pBr/Ad.1ITR-Sal (16.7) (ECACC deposit P97082118)

pBr/Ad.1ITR-Sal (9.4) is digested with SalI and dephosphorylated (TSAP, Life Technologies). To extend this clone up to the third SalI site in Ad5, pBr/Ad.Cla-Bam was linearized with BamHI and partially digested with SalI. A 7.3 kb SalI fragment containing adenovirus sequences from 9462–16746 was isolated in LMP agarose gel and ligated to the SalI-digested pBr/Ad.1ITR-Sal (9.4) vector fragment.

pWE/Ad.AflII-EcoRI pWE.pac was digested with ClaI and 5' protruding ends were filled using Klenow enzyme. The DNA was then digested with PacI and isolated from agarose gel. pWE/AflII-rITR was digested with EcoRI and after treatment with Klenow enzyme digested with PacI. The large 24 kb fragment containing the adenoviral sequences was isolated from agarose gel and ligated to the ClaI-digested and blunted pWE.pac vector using the Ligation Express™ kit (Clontech). After transformation of Ultracompetent XL 10-Gold cells from Stratagene, clones were identified that contained the expected insert. pWE/AflII-EcoRI contains Ad5 sequences from bp 3534–27336.

Construction of New Adapter Plasmids

The absence of sequence overlap between the recombinant adenovirus and E1 sequences in the packaging cell line is essential for safe, RCA-free generation and propagation of new recombinant viruses. The adapter plasmid pMLPI.TK is an example of an adapter plasmid designed for use according to the invention in combination with the improved packaging cell lines of the invention. This plasmid was used as the starting material to make a new vector in which nucleic acid molecules comprising specific promoter and gene sequences can be easily exchanged. First, a PCR fragment was generated from pZipΔMo+PyF101 (N⁻) template DNA (described in WO 96/35798) with the following primers: LTR-1:5'-CTG TAC GTA CCA GTG CA TGG CCT AGG CAT GGA AAA ATA CAT AAC TG-3' (SEQ. ID NO. 4) and LTR-2:5'-GCG GAT CCT TCG AAC CAT GGT AAG CTT GGT ACC GCT AGC GTT AAC CGG GCG ACT CAG TCA ATC G-3' (SEQ. ID NO. 5). Pwo DNA polymerase (Boehringer Mannheim) was used according to manufacturers protocol with the following temperature cycles: once 5' at 95° C.; 3' at 55° C.; and 1' at 72° C., and 30 cycles of 1' at 95° C., 1' at 60° C., 1' at 72° C., followed by once 10' at 72° C. The PCR product was then digested with BamHII and ligated into pMLP 10 (Levrero et al. 1991) vector digested with PvuII and BamHI, thereby generating vector pLTR10. This vector contains adenoviral sequences from bp 1 up to bp 454 followed by a promoter consisting of a part of the Mo-MuLV LTR having its wild-type enhancer sequences replaced by the enhancer from a mutant polyoma virus (PyF101). The promoter fragment was designated L420. Next, the coding region of the murine HSA gene was inserted. pLTR10 was digested with BstBI followed by Klenow treatment and digestion with NcoI. The HSA gene was obtained by PCR amplification on pUCl8-HSA (Kay et al. 1990) using the following primers:HSA1, 5'-GCG CCA CCA TGG GCA GAG CGA TGG TGG C-3' (SEQ. ID NO. 6) and HSA2,5 '-GTT AGA TCT AAG CTT GTC GAC ATC GAT CTA CTA ACA GTA GAG ATG TAG AA-3'(SEQ. ID NO. 7). The 269 bp amplified fragment was subcloned in a shuttle vector using the NcoI and BglII sites. Sequencing confirmed incorporation of the correct coding sequence of the HSA gene, but with an extra TAG insertion directly following the TAG stop codon. The coding region of the HSA gene, including the TAG duplication was then excised as a NcoI (sticky)-SalI (blunt) fragment and cloned into the 3.5 kb NcoI (sticky)/BstBI (blunt) fragment from pLTR10, resulting in pLTR-HSA10.

Finally, pLTR-HSA10 was digested with EcoRI and BamHI after which the fragment containing the left ITR, packaging signal, L420 promoter and HSA gene was inserted into vector pMLPI.TK digested with the same enzymes and thereby replacing the promoter and gene sequences. This resulted in the new adapter plasmid pAd/L420-HSA that contains convenient recognition sites for various restriction enzymes around the promoter and gene sequences. SnaBI and AvrII can be combined with HpaI, NheI, KpnI, HindIII to exchange promoter sequences, while the latter sites can be combined with the ClaI or BamHI sites 3' from HSA coding region to replace genes in this construct.

Another adapter plasmid that was designed to allow easy exchange of nucleic acid molecules was made by replacing the promoter, gene and poly A sequences in pAd/L420-HSA with the CMV promoter, a multiple cloning site, an intron and a poly-A signal. For this purpose, pAd/L420-HSA was digested with AvrII and BglII followed by treatment with Klenow to obtain blunt ends. The 5.1 kb fragment with pBr322 vector and adenoviral sequences was isolated and ligated to a blunt 1570 bp fragment from pcDNA1/amp (Invitrogen) obtained by digestion with HhaI and AvrII followed by treatment with T4 DNA polymerase. This adapter plasmid was named pCLIP.

Generation of Recombinant Adenoviruses

To generate E1 deleted recombinant adenoviruses with the new plasmid-based system, the following constructs were prepared: a) An adapter construct containing the expression cassette with the nucleic acid of interest linearized with a restriction enzyme that cuts at the 3' side of the overlapping adenoviral genome fragment, preferably not containing any pBr322 vector sequences; and b) A complementing adenoviral genome construct pWE/Ad.AflII-rITR digested with PacI. These two DNA molecules were further purified by phenol/chloroform extraction and EtOH precipitation. Co-transfection of these plasmids into an adenovirus packaging cell line, generated recombinant replication deficient adenoviruses by a one-step homologous recombination between the adapter and the complementing construct.

Alternatively, instead of pWE/Ad.AflII-rITR other fragments, can be used, e.g., pBr/Ad.Cla-Bam digested with EcoRI and BamHI or pBr/Ad.AflII-BamHI digested with PacI and BamHI can be combined with pBr/Ad.Sal-rITR digested with SalI. In this case, three plasmids are combined and two homologous recombinations are needed to obtain a recombinant adenovirus. It is to be understood that those skilled in the art may use other combinations of adapter and complementing plasmids without departing from the present invention. A general protocol as outlined below and meant as a non-limiting example of the present invention has been performed to produce several recombinant adenoviruses using various adapter plasmids and the Ad.AflII-rITR fragment. Adenovirus packaging cells (PER.C6) were seeded in ~25 cm² flasks and the next day when they were at ~80% confluency, transfected with a mixture of DNA and lipofectamine agent (Life Techn.) as described by the manufacturer. Routinely, 40 µl lipofectamine, 4 µg adapter plasmid and 4 µg of the complementing adenovirus genome fragment AflII-rITR (or 2 µg of all three plasmids for the double homologous recombination) are used. Under these conditions transient transfection efficiencies of 50% (48 hrs post transfection) are obtained as determined with control transfections using a pAd/CMV-LacZ adapter. Two days later, cells are passaged to ~80 cm² flasks and further cultured. Approximately five (for the single homologous recombination) to eleven days (for the double homologous recombination) later a cytopathogenia effect (CPE) is seen, indicating that functional adenovirus has formed. Cells and medium are harvested upon full CPE and recombinant virus is released by freeze-thawing. An extra amplification step in an 80 cm² flask is routinely performed to increase the yield since at the initial stage the titers are found to be variable despite the occurrence of full CPE. After amplification, viruses are harvested and plaque purified on PER.C6 cells. Individual plaques are tested for viruses with active transgenes.

Besides replacements in the E1 region it is possible to delete or replace (part of) the E3 region in the adenovirus because E3 functions are not necessary for the replication, packaging and infection of the (recombinant) virus. This creates the opportunity to use a larger insert or to insert more than one gene without exceeding the maximum package size (approximately 105% of wt genome length). This can be done, e.g., by deleting part of the E3 region in the pBr/Ad.Bam-rITR clone by digestion with XbaI and religation. This removes Ad5 wt sequences 28592–30470 including all known E3 coding regions. Another example is the precise replacement of the coding region of gp19K in the E3 region with a polylinker allowing insertion of new sequences. This, 1) leaves all other coding regions intact and 2) obviates the need for a heterologous promoter since the transgene is driven by the E3 promoter and pA sequences, leaving more space for coding sequences. To this end, the 2.7 kb EcoRI fragment from wt Ad5 containing the 5' part of the E3 region was cloned into the EcoRI site of pBluescript (KS-) (Stratagene). Next, the HindIII site in the polylinker was removed by digestion with EcoRV and HincIII and subsequent religation. The resulting clone pBS.Eco-Eco/ad5DHIII was used to delete the gp19K coding region. Primers 1 (5'-GGG TAT TAG GCC AA AGG CGC A-3') (SEQ. ID NO. 8) and 2 (5'-GAT CCC ATG GAA GCT TGG GTG GCG ACC CCA GCG-3') (SEQ. ID NO. 9) were used to amplify a sequence from pBS.Eco-Eco/Ad5DHIII corresponding to sequences 28511 to 28734 in wt Ad5 DNA. Primers 3 (5'-GAT CCC ATG GGG ATC CTT TAC TAA GTT ACA AAG CTA-3') (SEQ. ID NO. 10) and 4 (5'-GTC GCT GTA GTT GGA CTG G-3') (SEQ. ID NO. 11) were used on the same DNA to amplify Ad5 sequences from 29217 to 29476. The two resulting PCR fragments were ligated together by virtue of the new introduced NcoI site and subsequently digested with XbaI and MunI. This fragment was then ligated into the pBS.Eco-Eco/ad5ΔHIII vector that was digested with XbaI (partially) and MunI generating pBS.Eco-Eco/ad5ΔHIII.A gp19K. To allow insertion of foreign genes into the HindIII and bamHI site, an XbaI deletion was made in pBS.Eco-Eco/ad5ΔHIII.iΔgp19K to remove the BamHI site in the Bluescript polylinker. The resulting plasmid pBS.Eco-Eco/ad5ΔHIIIΔgp19KΔXbaI, contains unique HindII and BamHI sites corresponding to sequences 28733 (HindIII) and 29218 (BamHI) in Ad5. After introduction of a foreign gene into these sites, either the deleted XbaI fragment is reintroduced, or the insert is recloned into pBS.Eco-Eco/ad5ΔHIII.Δgp19K using HindIII and for example MunI. Using this procedure, we have generated plasmids expressing HSV-TK, hIL-la, rat IL-3, luciferase or LacZ. The unique SrfL and NotI sites in the pBS.Eco-Eco/ad5ΔHIII.Δgp19K plasmid (with or without inserted gene of interest) are used to transfer the region comprising the gene of interest into the corresponding region of pBr/Ad.Bam-rITR, yielding construct pBr/Ad.Bam-rITRΔ.gp19K (with or without inserted gene of interest). This construct is used as described supra to produce recombinant adenoviruses. In the viral context, expression of inserted genes is driven by the adenovirus E3 promoter.

Recombinant viruses that are both E1 and E3 deleted are generated by a double homologous recombination procedure as described above for E1-replacement vectors using a plasmid-based system consisting of:

a) an adapter plasmid for E1 replacement according to the invention, with or without insertion of a first gene of interest, b) the pWE/Ad.AflII-EcoRI fragment, and c) the pBr/Ad.Bam-rITRΔgp19K plasmid with or without insertion of a second gene of interest.

In addition to manipulations in the E3 region, changes of (parts of) the E4 region can be accomplished easily in pBr/Ad.Bam-rITR. Generation and propagation of such a virus, however, in some cases demands complementation in trans.

Example 2. Generation of Adenovirus Serotype 5 Based Viruses with Chimeric Fiber Proteins The method described infra to generate recombinant adenoviruses by co-transfection of two, or more separate cloned adenovirus sequences. One of these cloned adenovirus. sequences was modified such that the adenovirus serotype 5 fiber DNA was deleted and substituted for unique restriction sites thereby generating 'template clones' which allow for the easy introduction of DNA sequences encoding for fiber protein derived from other adenovirus serotypes. Generation of Adenovirus Template Clones Lacking DNA Encoding for Fiber The fiber coding sequence of adenovirus serotype 5 is located between nucleotides 31042 and 32787. To remove the adenovirus serotype 5 DNA encoding fiber we started with construct pBr/Ad.Bam-rITR. First an NdeI site was removed from this construct. For this purpose, pBr322 plasmid DNA was digested with NdeI after which protruding ends were filled using Klenow enzym. This pBr322 plasmid was then re-ligated, digested with NdeI and transformed into E. coli DH5α. The obtained pBr/ΔNdeI plasmid was digested with ScaI and SalI and the resulting 3198 bp vector fragment was ligated to the 15349 bp ScaI-SalI fragment derived from pBr/Ad.BamrITR, resulting in plasmid pBr/Δd.Bam-rITRΔNdeI which hence contained a unique NdeI site. Next a PCR was performed with oligonucleotides NY-up: 5'-CGA CAT ATG TAG ATG CAT TAG TTT GTG TTA TGT TTC AAC GTG-3' (SEQ. ID NO. 12) and NY-down: 5'-GGA GAC CAC TGC CAT GTT-3' (SEQ. ID NO. 13). During amplification, both an NdeI (bold face) and an NsiI restriction site (underlined) were introduced to facilitate cloning of the amplified fiber DNAs. Amplification consisted of 25 cycles of each 45 sec. at 94° C., 1 min. at 60° C., and 45 sec. at 72° C. The PCR reaction contained 25 pmol of oligonucleotides NY-up or NY-down, 2 mM dNTP, PCR buffer with 1.5 mM MgCl$_2$, and 1 unit of Elongase heat stable polymerase (Gibco, The Netherlands). One-tenth of the PCR product was run on an agarose gel that demonstrated that the expected DNA fragment of ±2200 bp was amplified. This PCR fragment was subsequently purified using Geneclean kit system (Bio 101 Inc). Then, both the construct pBr/Ad.Bam-rITRΔNdeI as well as the PCR product were digested with restriction enzymes NdeI and Sbf I. The PCR fragment was subsequently cloned using T4 ligase enzyme into the NdeI and Sbf I digested pBr/Ad.Bam-rITRΔNdeI, generating pBr/Ad.BamRΔFib. This plasmid allows insertion of any PCR amplified fiber sequence through the unique NdeI and NsiI sites that are inserted in place of the removed fiber sequence. Viruses can be generated by a double homologous recombination in packaging cells described infra using an adapter plasmid, construct pBr/Ad.AflII-EcoRI digested with PacI and EcoRI and a pBr/Ad.BamRΔFib construct in which heterologous fiber sequences have been inserted. To increase the efficiency of virus generation, the construct pBr/Ad.BamRΔFib was modified to generate a PacI site flanking the right ITR. Hereto, pBr/Ad.BamRΔFib was digested with AvrII and the 5 kb adenofragment was isolated and introduced into the vector pBr/Ad.Bam-rITR.pac#8 replacing the corresponding AvrII fragment. The resulting construct was named pBr/Ad.BamRΔFib.pac. Once a heterologous fiber sequence is introduced in pBr/Ad.BamRΔFib.pac, the fiber modified right hand adenovirus clone may be introduced into a large cosmid clone as described for pWE/Ad.AflII-rITR in example 1. Such a large cosmid clone allows generation of adenovirus by only one homologous recombination making the process extremely efficient.

Amplification of Fiber Sequences from Adenovirus Serotypes

To enable amplification of the DNAs encoding fiber protein derived from alternative serotypes degenerate oligonucleotides were synthesized. For this purpose, first known DNA sequences encoding for fiber protein of alternative serotypes were aligned to identify conserved regions in both the tail-region as well as the knob-region of the fiber protein. From the alignment, which contained the nucleotide sequence of 19 different serotypes representing all 6 subgroups, (degenerate) oligonucleotides were synthesized (see Table II). Also shown in Table II is the combination of oligonucleotides used to amplify the DNA encoding fiber protein of a specific serotype. The amplification reaction (50 μl) contained 2 mM dNTPs, 25 pmol of each oligonucleotide, standard 1× PCR buffer, 1, 5 mM MgCl$_2$, and 1 Unit Pwo heat stable polymerase (Boehringer) per reaction. The cycler program contained 20 cycles, each consisting of 30 sec. 94° C., 60 sec. 60–64° C., and 120 sec. At 72° C., 10% of the PCR product was run on an agarose gel which demonstrated that a DNA fragment was amplified. Of each different template, two independent PCR reactions were performed after which the independent PCR fragments obtained were sequenced to determine the nucleotide sequence. From 11 different serotypes, the nucleotide sequence could be compared to sequences present in Genbank. Of all other serotypes, the DNA encoding fiber protein was previously unknown and was therefore aligned with known sequences from other subgroup members to determine homology i.e. sequence divergence. Of the 51 human serotypes known to date, all fiber sequences, except for serotypes 1, 6, 18, and 26, have been amplified and sequenced.

Generation of Fiber Chimeric Adenoviral DNA Constructs

All amplified fiber DNAs as well as the vector (pBr/Ad.BamRΔFib) were digested with NdeI and NsiI. The digested DNAs were subsequently run on a agarose gel after which the fragments were isolated from the gel and purified using the Geneclean kit (Bio 101 Inc). The PCR fragments were then cloned into the NdeI and NsiI sites of pBr/AdBamRΔFib, thus generating pBr/AdBamRFibXX (where XX stands for the serotype number of which the fiber DNA was isolated). So far the fiber sequence of serotypes 5/ 7/ 8/ 9/ 10/ 11/ 12/ 13/ 14/ 16/ 17/ 19/21/24/27/28/29/ 30/ 32/ 33/34/35/ 36/37/ 38/ 40-s/ 40-L/ 41-S/ 42/ 45/ 47/ 49/ 51 have been cloned into pBr/AdBamRFibXX. From pBr/AdBamRFibXX (where XX is 5/ 8/ 9/ 10/ 11/ 13/ 16/ 17/ 24/ 27/ 30/ 32/ 33/ 34/ 35/ 38/ 40-S/ 40-L/ 45/ 47/ 49/ 51) a cosmid clone in pWE/Ad.AflII-rITR (see example 1) was generated to facilitate efficient virus generation. This cosmid cloning resulted in the formation of construct pWE/Ad.AflII-rITR/FibXX (where XX stands for the serotype number of which the fiber DNA was isolated).

Generation of Recombinant Adenovirus Chimeric For Fiber Protein

To generate recombinant adenovirus carrying the fiber of serotype 12, 16, 28, 40-L, 51, and 5, three constructs, pCLIP/luciferase, pWE/AdAflII-Eco and pBr/AdBamrITR.pac/fibXX (XX=12, 16, 28, 40-L, 51, and 5) were transfected into adenovirus producer cells. To generate recombinant Ad 5 virus carrying the fiber of 5/ 7/ 8/ 9/ 10/ 11/ 12/ 13/ 14/ 16/ 17/ 19/21/ 24/ 27/28/29/ 30/ 32/ 33/ 34/ 35/ 36/ 37/38/ 40-S/ 40-L/ 41-S/ 42/ 45/ 47/ 49/ 51, two constructs, pCLIP/luciferase and pWE/Ad.AflII-rITR/FibXX were transfected into adenovirus producer cells. For transfection, 2 μg of pCLIP/luciferase, and 4 μg of both pWE/AdAflII-Eco and pBr/AdBamrITR.pac/fibXX (or in case of cosmids; 4 μg of pCLIP/luciferase plus 4 μg of pWE/Ad.AflII-rITR/FibXX) were diluted in serum free DMEM to 100 μl total volume. To this DNA suspension 100 μl 1× diluted Lipofectamine (Gibco) was added. After 30 min at room temperature the DNA-lipofectamine complex solution was added to 2.5 ml of serum-free DMEM which was subsequently added to a T25 cm$^2$ tissue culture flask. This flask contained 2×10$^6$ PER.C6 cells that were seeded 24-hours prior to transfection. Two hours later, the DNA-lipofectamine complex containing medium was diluted once by the addition of 2.5 ml DMEM supplemented with 20% fetal calf serum. Again 24 hours later the medium was replaced by fresh DMEM supplemented with 10% fetal calf serum. Cells were cultured for 6–8 days, subsequently harvested, and freeze/thawed 3 times. Cellular debris was removed by centrifugation for 5 min at 3000 rpm room temperature. Of the supernatant (12.5 ml) 3–5 ml was used to infect again infect PER.C6 cells (T80 cm$^2$ tissue culture flasks). This re-infection results in full cytopathogenic effect (CPE) after 5–6 days after which the adenovirus is harvested as described above. Besides the construction and generation of fiber-chimeric vectors carrying only luciferase as a marker gene as described above, many fiber-chimeric viruses were generated carrying other marker genes by using pCLIP or pAdapt as adapter plasmids in which for instance LacZ or green fluorescent protein (GFP) were cloned in the polylinker present in these plasmids. Here, pCLIP/LacZ and pAdapt.GFP were used to generate recombinant adenoviruses expressing the respective transgenes (these different adapter plasmids are described above and in WO 99/55132, WO 00/63403 and WO 01/20014).

Example 3. Production, purification, and Titration of Fiber Chimeric Adenoviruses Of the supernatant obtained from transfected PER.C6 cells 10 ml was used to inoculate a 1 l fermentor which contained $1-1.5 \times 10^6$ cells/ml PER.C6 that were specifically adapted to grow in suspension. Three days after inoculation, the cells were harvested and pelleted by centrifugating for 10 min. at 1750 rpm at room temperature. The chimeric adenoviruses present in the pelleted cells were subsequently extracted and purified using the following downstream processing protocol. For small scale productions adherent PER.C6 cells were used in combination with T175 $cm^2$ tissue culture flasks. Irrespective of the scale of the production cells were treated identically. The pellet was dissolved in 50 ml 10 mM $NaPO_4$ and frozen at $-20°$ C. After thawing at $37°$ C., 5.6 ml deoxycholate (5% w/v) was added after which the solution was homogenized. The solution was subsequently incubated for 15 min. at $37°$ C. to completely crack the cells. After homogenizing the solution, 1875 µl (1M) $MgCl_2$ was added and 5 ml 100% glycerol. After the addition of 375 µl DNAse (10 mg/ml) the solution was incubated for 30 min. at $37°$ C. Cell debris was removed by centrifugation at 1880 g for 30 min. at room temperature without the brake on. The supernatant was subsequently purified from proteins by loading on 10 ml of freon. Upon centrifugation for 15 min. at 2000 rpm without brake at room temperature three bands are visable of which the upper band represents the adenovirus. This band was isolated by pipetting after which it was loaded on a Tris/HCl (1M) buffered cesium chloride blockgradient (range: 1.2 to 1.4 g/ml). Upon centrifugation at 21,000 rpm for 2.5 h at $10°$ C. the virus was purified from remaining protein and cell debris since the virus, in contrast to the other components, does not migrate into the 1.4 g/ml cesium chloride solution. The virus band is isolated after which a second purification using a Tris/HCl (1M) buffered continues gradient of 1.33 g/ml of cesium chloride is performed. After virus loading on top of this gradient the virus is centrifuged for 17 h at 55000 rpm at $10°$ C. Subsequently the virus band is isolated and after the addition of 30 µl of sucrose (50 w/v) excess cesium chloride is removed by three rounds of dialysis, each round comprising of 1 h. For dialysis the virus is transferred to dialysis slides (Slide-a-lizer, cut off 10,000 kDa, Pierce, USA). The buffers used for dialysis are PBS which are supplemented with an increasing concentration of sucrose (round 1 to 3:30 ml, 60 ml, and 150 ml sucrose (50% w/v)/ 1.5 liter PBS, all supplemented with 7.5 ml 2% (w/v) $CaMgCl_2$). After dialysis, the virus is removed from the slide-a-lizer after which it is aliquoted in portions of 25 and 100 µl upon which the virus is stored at $-85°$ C. To determine the number of virus particles per ml, 100 µl of the virus batch is run on a high pressure liquid chromatograph (HPLC). The adenovirus is bound to the column (anion exchange) after which it is eluted using a NaCl gradient (range 300–600 mM). Thy determining the area under the virus peak the number of virus particles can be calculated. To determine the number of infectious units (1 U) per ml present in a virus batch, titrations are performed on 911 cells. For this purpose, $4 \times 10^4$ 911 cells are seeded per well of 96-well plates in rows B, D, and F in a total volume of 100 µl.per well. Three hours after seeding the cells are attached to the plastic support after which the medium can be removed. To the cells a volume of 200 µl is added, in duplicate, containing different dilutions of virus (range: $10^2$ times diluted to $2 \times 10^9$). By screening for CPE the highest virus dilution that still renders CPE after 14 days is considered to contain at least one infectious unit. Using this observation, together with the calculated amount of virus volume present in these wells renders the number of infectious units per ml of a given virus batch. The production results i.e. virus particles per ml of chimeric adenoviruses with the luciferase cDNA as a marker, are shown in Table II.

Example 4. Expression of Integrins and CAR on Human Primary Chondrocytes

To test for expression on primary chondrocytes for membrane molecules known to be involved in Ad5 infection, the presence of CAR, and $a_v$-integrins was assayed on a flow cytometer. Since the MRC class I alpha-2 domain has also been proposed as a receptor for Ad5, expression of this molecule was tested as well. For this purpose $2 \times 10^4$ chondrocytes were washed once with PBS/0.5% BSA after which the cells were centrifuged for 5 min. at 1750 rpm at room temperature.

Subsequently, 10 µl of a 100 times diluted $a_v b3$ antibody (Mab 1961, Brunswick chemie, The Netherlands), a 100 times diluted antibody ab5 (antibody (Mab 1976, Brunswick chemie, The Netherlands), or 1000 times diluted CAR (Hsu et al. 1988) antibody (a kind gift of Dr. Bergelson, Harvard Medical School, USA) was added to the cell pellet after which the cells were incubated for 30 min. at $4°$ C. in a dark environment. After this incubation, cells were washed twice with PBS/0.5% BSA and again pelleted by centrifugation for 5 min. at 1750 rpm room temperature. To label the cells, 10 ml of rat antimouse IgGl labeled with phycoerythrine (PE) was added to the cell pellet upon which the cells were again incubated for 30 min. at $4°$ C. in a dark environment. Finally the cells were washed twice with PBS/0.5% BSA and analyzed on a flow cytometer. The results of these experiments are shown in FIG. 1. From the results it can be concluded that primary human chondrocytes do not express detectable levels of CAR that is the primary receptor for Ad5. The cells do express MHC-class I, but since this is a very low affinity receptor, the results confirm that chondrocytes are difficult to transduce with an adenovirus serotype 5.

Example 5. Adenovirus Transduction of Human Primary Chondrocytes

Figure 2A:
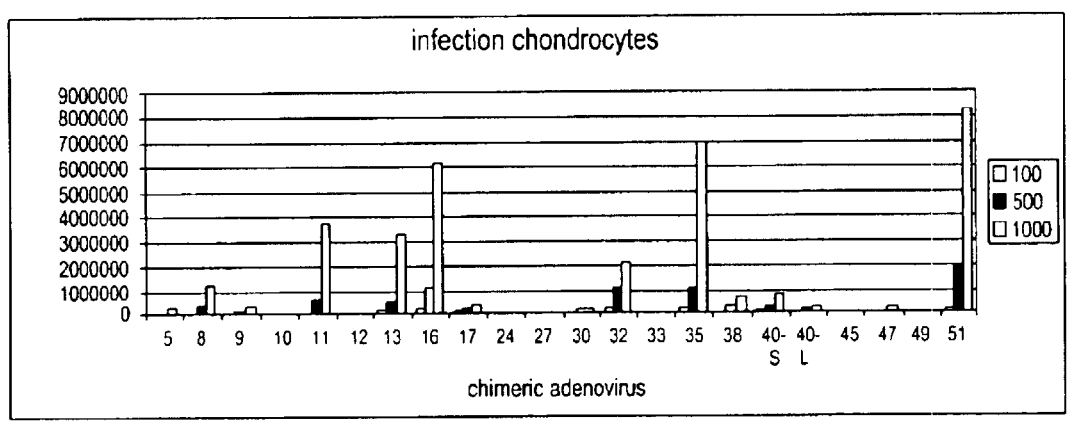
FIG. 2: Screening the fiber chimeric viruses for the presence of viruses that are better suited for transduction of primary human chondrocytes. The doses used are 100, 500 or 1000 virus particles per cell. Luciferase activity is expressed in relative light units (RLU). (A) and (B) represent two separate independent experiments performed on chondrocytes derived from different donors.
Figure 2B:
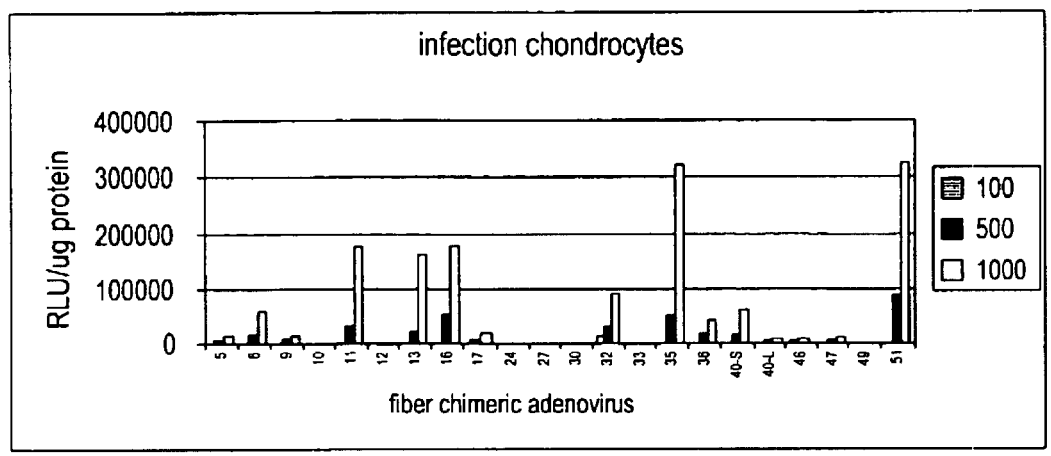

Human primary chondrocytes were cultured in Dulbecco's modified Eagles medium (DMEM) supplemented with 10% fetal calf serum and further supplemented with essential amino acids (proline 0.4 mM), non-essential amino acids (1×), cholic acid-6-phosphate (0.2 mM) and buffered with HEPES (10 nM) (all materials derived from Gibco). In a first experiment, $10^5$ chondrocytes were seeded in wells of 24-well plates. The next day cells were exposed to either 100, 500, or 1000 virus particles per cell of recombinant fiber chimeric viruses carrying the fiber of serotype 8, 9, 10, 11, 12, 13, 16, 17, 24, 27, 30, 32, 33, 35, 38, 40-S, 40-L, 45, 47, 49, or 51. In these experiments, the parent vector (fib5) was taken along as a reference. Forty-eight hours after the addition of virus, cells were washed twice with 1 ml PBS after which cells were lysed by adding 100 µl of cell lysis buffer. Lysates were subsequently transferred to 96-well plates and stored at −20 degrees Celsius until luciferase activity measurement. Luciferase activity was determined using a bioluminescence machine, the luciferase assay kit from Promega™ (catalog no. E-1501) and the instructions provided by the manufacturer. The results of the luciferase transgene expression measured in primary human chondrocytes after transduction with the panel of fiber chimeric viruses is shown in FIGS. 2A and B (chondrocytes derived from two individual donors). The results demonstrate that several fiber chimeric viruses perform better on chondrocytes as compared to the parent vector (Ad5). These viruses carry the fiber from a subgroup B viruses i.e. 11, 16, 35, and 51. Also, several, but not all, viruses carrying a fiber originating from subgroup D i.e. 8, 13, and 32 are better equipped for transducing chondrocytes. These results thus clearly show that from a library containing different fiber-chimeric vectors, adenoviruses can be identified that are improved in their ability to transduce human cell types of interest, i.e. chondrocytes. Moreover, these results demonstrate that human adenoviruses, between subgroups but even within a subgroup, can recognize distinct attachment molecules on human cells.

Example 6. Effect of Adenovirus Transduction on Human Chondrocytes

Figure 3A:
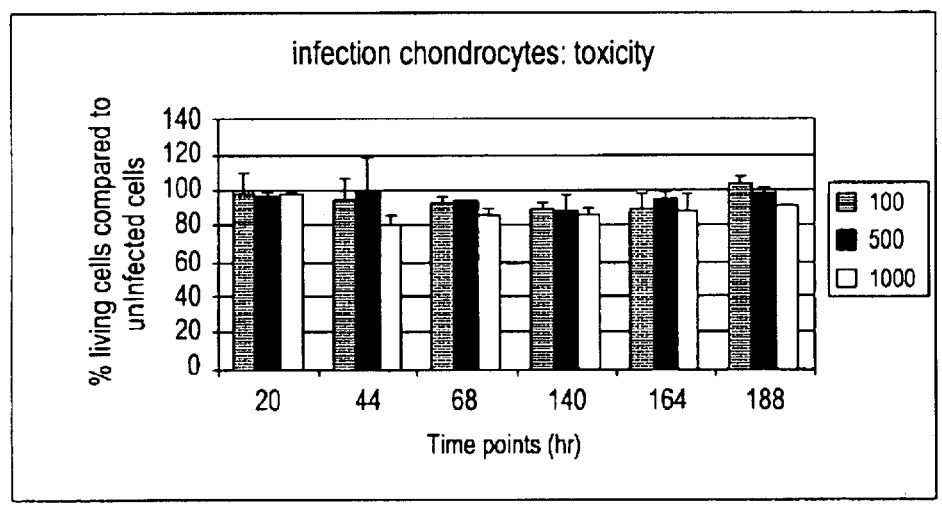
FIG. 3: (A) Effect of adenoviral infection on chondrocyte viability. Three different moi's of a LacZ expressing virus (Ad5Fib16LaCZ, generated with pCIJP.LacZ as adapter plasmid) were used to infect human primary chondrocytes. Viability was checked at several time points following the infection. (B) Duration of LacZ expression in transfected human chondrocytes.

To determine the effect of infection by adenovirus in time on chondrocytes in terms of toxicity, human primary chondrocytes were seeded 24 h prior to infection in a density of $5 \times 10^4$ cells/well in a 24 well dish. Cells were infected with one of the improved viruses identified, i.e. Ad5Fib16. Chondrocytes were infected with Ad5Fib16LacZ using moi' s of 100, 1000 and 5000 vp/cell. The viruses remained in the solution throughout the experiment. LacZ expression was monitored at different time points: 20, 44, 68, 140, 164 and 188 post infection. The viability of the cells was determined by using the MTS assay from Promega using the instructions provided by the manufacturer. In general, 200 µl of the so-called Cell Titer Aqueous One Solution Reagent was added to the well and incubated for 4 h at 37° C. This was followed by inactivation of the virus and stopping the reaction by adding 25 µl 10% SDS solution. 100 µl of the mixture was transferred to a well in a 96-well dish and absorbance was measured at 490 nm and compared to the controls. Every time point experiment was performed in triplicate and averaged. The results are shown in FIG. 3A and indicate that the human primary chondrocytes do not suffer significantly from the adenoviral infections, even when an high moi of 5000 virus particles per cell was applied.

Figure 3B:
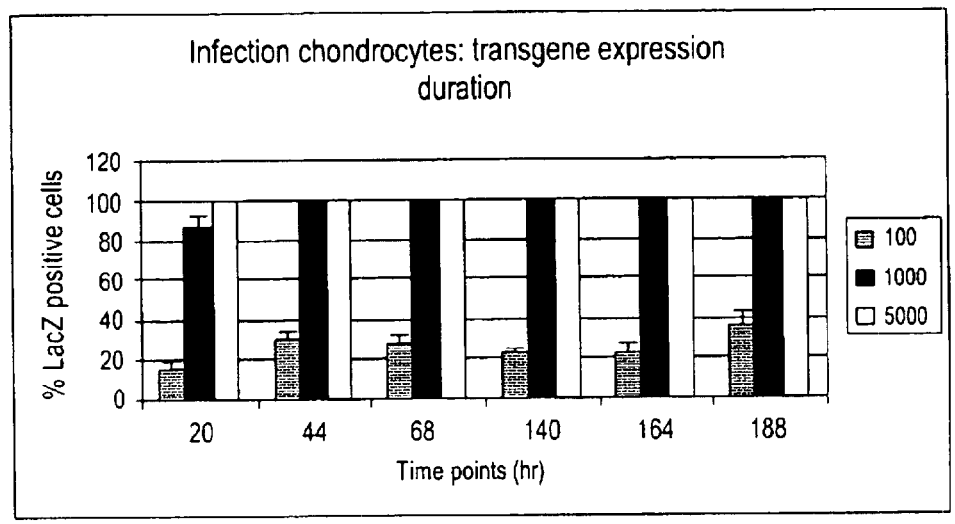

Cells that were infected in an identical manner as described above, were used to determine the expression of the LacZ transgene over time. For this, cells were washed twice with PBS and fixed with 0.5 ml/well of a fixative solution (1.08 ml formaldehyde (JT Baker) plus 480 µl Glutar-dialdehyde (Merck) in 40 ml PBS) and incubated for 10 min. at room temperature. Then, cells were washed twice with PBS and stained with 0.5 ml/well staining solution (1 ml $K_3Fe(CN)_6$, 1 ml $K_4Fe(CN)_6$, 80 µl 1M $MgCl_2$, filled up to 40 ml with PBS, to which 150 µl X-Gal per 6 ml is added prior to use) for 4 h at 37° C. Positive cells were counted and compared to negative cells. The results are shown in FIG. 3B and indicate that over prolonged periods of time the transgene expression is not significantly diminished in human primary chondrocytes upon infection with adenovirus. The latter results indicate that sufficient vector copies are present in the nucleus of transduced chondrocytes to allow for at least 4 cell doublings without losing the marker gene.

Figure 4A:
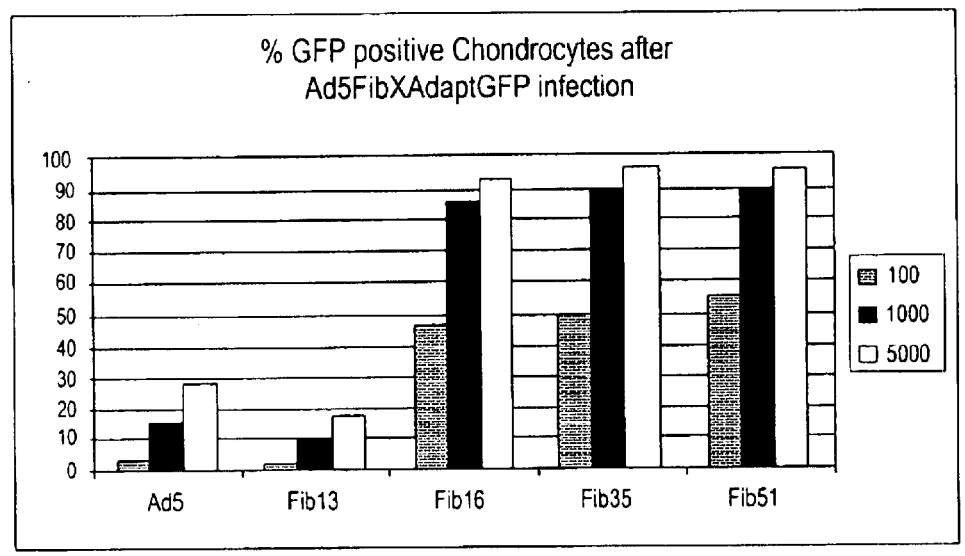
FIG. 4: (A) Flow cytometric analysis of chondrocytes exposed to different adenoviral vectors. Non-transduced chondrocytes were used to set the flow cytometric background at 1% Green Fluorescent Protein (GFP) positive cells. Shown is the percentage of chondrocytes in the cell population that became positive for GFP after infection with GFP expressing recombinant adenoviruses (X in AdFibXAdaptGFP stands for different fibers derived from different serotypes in a Ad5 backbone generated with pAdApt as adapter plasmid). (B) Shown is the median fluorescence that indicates the amount of GFP produced per cell.
Figure 4B:
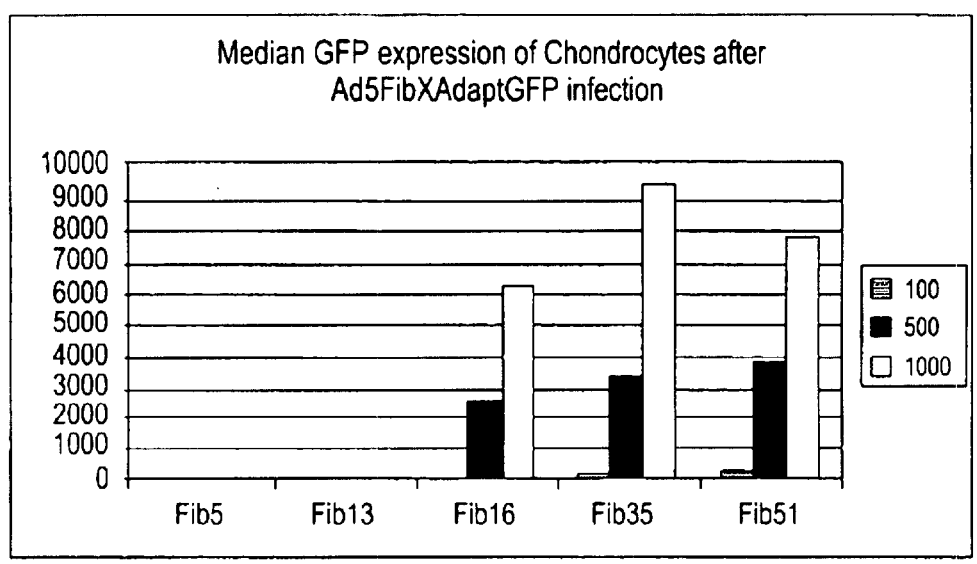

Example 7. Expression of Green Fluorescent Protein in Human Chondrocytes Upon Infection by Adenovirus Although both luciferase and LacZ provide data concerning the transduction efficiency of Ad5 and fiber-chimeric vectors in chondrocytes determination on a single cell level is difficult using these marker genes. Therefore, we compared Ad5 with Ad5Fib13, Ad5Fib16, Ad5Fib35, and Ad5Fib51 viruses all carrying green fluorescent protein (GFP) as a marker gene. Detection of GFP expression can be monitored using a flow cytometer (FACScalibur, Becton Dickinson). Hereto, human primary chondrocytes were seeded 24 h prior to infection in a density of $5 \times 10^4$ cells/well in a 24 well dish. Cells were exposed for 2 h to the vectors at a concentration 100, 500, 1000, virus particles per cell. Forty-eight hours after virus exposure cells were harvested and subjected to flow cytometric analysis. To set the flow cytometer, non-transduced chondrocytes were used (background gate 1% positive cells). Subsequently, cells exposed to the different adenoviral vectors were assayed. As shown in FIG. 4A, the percentage of cells positive for GFP increased using an increase in viral load from 100 to 1000 virus particles per cell. Moreover, the results show that using Ad5Fib16, Ad5Fib35, or Ad5Fib51 the amount of cells transduced is increased drastically as compared to cells exposed to Ad5. (3–9 fold more cells dependent on MOI). Besides the increase in the number of cells that became positive for GFP using the fiber-chimeric vectors another parameter was also monitored, i.e. median fluorescence. This parameter gives information concerning the amount of GFP produced on a single cell level. Results of this analysis is shown in FIG. 4B as demonstrates that the amount of GFP produced per cell is much higher using Ad5Fib16, Ad5Fib35, or Ad5Fib51 as compared to Ad5. Thus, using these fiber-chimeric vectors both the amount of cells transduced as well as the amount of vector copies per cell is significantly increased.

REFERENCES

Amin A R, Attur M and Abramson S B (1999) Nitric oxide synthase and cyclooxygenase: distribution, regulation and intervention in arthritis. Curr Opin Rheumatol 11: 202–209.

Arnberg N, Mei Y and Wadell G (1997) Fiber genes of adenoviruses with tropism for the eye and the genital tract. Virology 227: 239–244.

Bout A (1996) Prospects for human gene therapy. Eur J Drug Met and Pharma 2: 175–179.

Blaese M, Blankenstein T, Brenner M, Cohen-Hagenauer O, Gansbacher B, Russel S, Sorrentino B and Velu T (1995) Cancer Gene Ther 2: 291–297.

Brody S L and Crystal R G (1994) Adenovirus mediated in vivo gene transfer. Ann NY Acad Sci 716: 90–101.

Chroboczek J, Ruigrok R W H and Cusack S (1995) Adenovirus fiber, p. 163–200. In: W. Doerfler and P. Bohm (ed.), The molecular repertoire of adenoviruses, I. Springer-Verlag, Berlin.

De Jong J C, Wermenbol A G, Verweij-Uijterwaal M W, Slaterus K W, Wertheim-Van Dillen P, Van Doomum G J, Khoo S H and Hierholzer J C (1999) Adenoviruses from human immunodeficiency virus-infected individuals, including two strains that represent new candidate serotypes Ad50 and Ad51 of species B1 and D, respectively. J Clin Microbiol 37: 3940–3945.

Defer C, Belin M, Caillet-Boudin M and Boulanger P (1990) Human adenovirus-host cell interactions; comparative study with members of subgroup B and C. J Virology 64: 3661–3673.

Fernandez J, Tardif G, Martel-pelletier J. Lascau-Coman V, Dupuis M, Moldovan F, Sheppard M, Krishnan B R, Pelletier J P (1999) In vivo transfer of interleukin-1 receptor antagonist gene in osteoarthritic rabbit knee joints: prevention of osteoarthritis progression. Am J Pathol 154: 1159–1169.

Francki R I B, Fauquet C M, Knudson D L and Brown F (1991) Classification and nomenclature of viruses. Fifth report of the international Committee on taxonomy of viruses. Arch Virol Suppl 2: 140–144.

Frenkel S R and DiCesare P E (1999) Degradation and repair of articular cartilage. Front Biosci 15: 671–685.

Gazit D, Turgeman G, Kelley P, Wang E, Jalenak M, Zilberman Y and Moutsatsos I (1999) Engineered pluripotent mesenchymal cells integrate and differentiate in regenerating bone: a novel cell-mediated gene therapy. J Gene Med 1: 121–133.

Goto H, Shuler F D, Lamsam C, Moller H D, Niyibiz C, Fu F U, Robbins P D and Evans C H (1999) Transfer of LacZ marker gene to the meniscus. J Bone Joint Surg Am 81: 918–925.

Greber U F, Willets M, Webster P and Helenius A (1993) Stepwise dismanteling of adenovirus 2 during entry into cells. Cell 75: 477–486.

Hynes R O (1992) Integrins: versatility, modulation and signalling in cell adhesion. Cell 69: 11–25.

Hierholzer J C, Wigand R, Anderson L J, Adrian T and Gold J W M (1988) Adenoviruses from patients with AIDS: a plethora of serotypes and a description of five new serotypes of subgenus D (types 43–47). J Infect Dis 158: 804–813.

Hierholzer J C (1992) Adenovirus in the immunocompromised host. Clin Microbiol Rev 5: 262–274.

Hsu K H, Lonberg-Holm K, Alstein B and Crowell R L (1989) A monoclonal antibody specific for the cellular receptor for the group B coxsackieviruses. J Virol 62: 1647–1652.

Ishibashi M and Yasue H (1984) The adenoviruses, H. S. Ginsberg, ed., Plenum Press, Londen, New York. Chapter 12: 497–561.

Kay R, Takei F and Humphries R K (1990) Expression cloning of a cDNA encoding M1/69. J Immunol 145: 1952–1959.

Khoo S H, Bailey A S, De Jong J C and Mandal B K (1995) Adenovirus infections in human immunodeficiency virus-positive patients: Clinical features and molecular epidemiology. J Infect Dis 172: 629–637.

Kidd A H, Chroboczek J, Cusack S and Ruigrok R W (1993) Adenovirus type 40 virions contain two distinct fibers. Virology 192: 73–84.

Kramer J, Hegert C, Guan K, Wobus A M, Muller P K and Rohwedel J (2000) Embryonic stem cell-derived chondrogenic differentiation in activation by BMP-2 and BMP-4. Mech Dev 92: 193–205.

Krasnykh V N, Mikheeva G V, Douglas J T and Curiel D T (1996) Generation of recombinant adenovirus vectors with modified fibers for altering viral tropism. J Virol 70: 6839–6846.

Levrero M, Barban V, Manteca S, Ballay A, Balsamo C, Avantaggiati M L, Natoli G, Skellekens H, Tiollais P, Perricaudet M (1991) Defective and nondefective adenovirus vectors for expressing foreign genes in vitro and in vivo. Gene 101: 195–202

Lubberts E, Joosten L A, Van den Bersselaar L, Helsen M M, Bakker A C Van Meurs J B, Graham J B, Richards C D and Van den Berg W B (1999) Adenoviral vector-mediated gene delivery to the temporomandibular joint in Guinea-pigs. Arch Oral Biol 44: 701–709.

Madry H and Trippel S B (2000) Efficient Lipid-mediated gene transfer to articular Chondrocytes. Gene Ther 7: 286–291.

Mason J M, Grande D A, Barcia M, Grant R, Pergolizzi R G and Breitbart A S (1998) Expression of human bone morphogenesis protein 7 in primary rabbit periosteal cells: potential utility in gene therapy for osteochondral repair. Gene Ther 5: 1098–1104.

Morgan C, Rozenkrantz H S and Mednis B (1969) Structure and development of viruses as observed in the electron microscope.X. Entry and uncoating of adenovirus. J Virol 4: 777–796.

Nishlda K, Kang J D, Gilbertson L G, Moon S H, Suh J K, Vogt M T, Robbins P D and Evans G H (1999) Modulation of the biological activity of the rabbit intervertebral disc by gene therapy: an in vivo study of adenovirus-mediated transfer of the human transforming growth factor beta 1 encoding gene. Spine 24: 2419–2425.

Pizette S and Niswander L (2000) BMPs are required at two steps of limb chondrogenesis: formation of prechondrogenic condensations and their differentiation into chondrocytes. Dev Biol 219: 237–249.

Richardson J B, Caterson B, Evans E H, Ashton B A and Roberts S (1999) Repair of human cartilage after implantation of autologous chondrocytes. J Bone Joint Surg Br 81: 1064–1068.

Roelvink P W, Lizonova A, Lee J G M, Li Y, Bergelson J M, Finberg R W, Brough D E, Kovesdi I and Wickham T J (1998) The coxsackie-adenovirus receptor protein can function as a cellular attachment protein for adenovirus serotypes from subgroups A, C, D, E, and F. J Virol 72: 7909–7915.

Schnurr D and Dondero M E (1993) Two new candidate adenovirus, serotypes. Intervirol 36: 79–83.

Silverman R P, Bonasser L, Passaretti D, Randolph M A and Yaremchuk M (2000) Adhesion of tissue-engineered cartilate to native cartilage. Plast Reconstr Surg 105: 1393–1398.

Signas G, Akusjarvi G and Petterson U (1985) Adenovirus 3 fiberpolypeptide gene: Complications for the structure of the fiber protein. J Virol 53: 672–678.

Stevenson S C, Rollence M, White B, Weaver L and McClelland A (1995) Human adenovirus serotypes 3 and 5 bind to two different cellular receptors via the fiber head domain. J Virol 69: 2850–2857.

Stevenson S C, Rollence M, Marshall-Neff J and McClelland A (1997) Selective targeting of human cells by a chimeric adenovirus vector containing a modified fiber protein. J Virology 71: 4782–4790.

Stouten P W F, Sander C, Ruigrok R W H and Cusack S (1992) New triple helical model for the shaft of the adenovirus fiber. J Mol Biol 226: 1073–1084.

Svensson V and Persson R (1984) Entry of adenovirus 2 into Hela cells. J Virol 51: 687–694.

Taniguchi K, Kohsaka H, Inoue N, Terada Y, Ito H, Hirokawa K and Miyasaka N (1999) Induction of the p16INK4a senescence gene as a new therapeutric strategy for the treatment of rheumatoid arthritis. Nat Med 5: 760–767.

Varga M J, Weibull C and Everitt E (1991) Infectious entry pathway of adenovirus type 2. J Virol 65: 6061–6070.

Whalen J D, Lechman E L, Carlos C A, Weiss K, Kovesdi I, Glorioso J C, Robbins P D and Evans C H (1999) Adenoviral transfer of the viral IL-10 gene periarticularly to mouse paws suppresses development of collagen-induced arthritis in both injected and uninjected paws. J Immunol 162: 3625–3632.

Wickham T J, Mathias P, Cheresh D A and Nemerow G R (1993) Integrins avb3 and avb5 promote adenovirus internalization but not virus attachment. Cell 73: 309–319.

TABLE 1

Association of different human adenovirus serotypes with human disease.

| Syndrome | Subgenus | Serotype |
|---|---|---|
| Respiratory illness | A | 31 |
|  | B | 3, 7, 11, 14, 21, 34, 35, 51 |
|  | C | 1, 2, 5, 6 |
|  | D | 39, 42–48 |
|  | E | 4 |
| Keratoconjunctivitis (eye) | B | 11 |
|  | D | 8, 19, 37, 50 |
| Hemorrhagic cystitis (Kidney) And urogenital tract infections | B | 7, 11, 14, 16, 21, 34, 35 |
|  | C | 5 |
|  | D | 39, 42–48 |
| Sexual transmission | C | 2 |
|  | D | 19, 37 |
| Gastroenteritis | A | 31 |
|  | B | 3 |
|  | C | 1, 2, 5 |
|  | D | 28 |
|  | F | 40, 41 |
| CNS disease | A | 12, 31 |
|  | B | 3, 7 |
|  | C | 2, 5, 6 |
|  | D | 32, 49 |
| Hepatitis | A | 31 |
|  | C | 1, 2, 5 |
| Disseminated | A | 31 |
|  | B | 3, 7, 11, 21 |
|  | D | 30, 43–47 |
| None (???) | A | 18 |
|  | D | 9, 10, 13, 15 17, 20, 22–29, 33, 36, 38 |

TABLE II

Production results of recombinant fiber chimeric adenoviruses. Results in virus particles per milliliter as determined by HPLC.

| Adenovirus | Virus particles/ml |
|---|---|
| Ad5Fib5 | $2.2 \times 10^{12}$ |
| Ad5Fib9 | $4.9 \times 10^{11}$ |
| Ad5Fib10 | $5.5 \times 10^{11}$ |
| Ad5Fib11 | $1.1 \times 10^{12}$ |
| Ad5Fib12 | $4.4 \times 10^{12}$ |
| Ad5Fib13 | $1.1 \times 10^{12}$ |
| Ad5Fib16 | $1.4 \times 10^{12}$ |
| Ad5Fib17 | $9.3 \times 10^{11}$ |
| Ad5Fib24 | $1.0 \times 10^{12}$ |
| Ad5Fib27 | $3.0 \times 10^{11}$ |
| Ad5Fib30 | $7.1 \times 10^{11}$ |
| Ad5Fib32 | $2.0 \times 10^{12}$ |
| Ad5Fib33 | $1.5 \times 10^{12}$ |
| Ad5Fib35 | $2.0 \times 10^{12}$ |
| Ad5Fib38 | $5.8 \times 10^{11}$ |
| Ad5Fib40-S | $3.2 \times 10^{10}$ |
| Ad5Fib40-L | $2.0 \times 10^{12}$ |
| Ad5Fib45 | $2.8 \times 10^{12}$ |
| Ad5Fib47 | $2.6 \times 10^{12}$ |
| Ad5Fib49 | $1.2 \times 10^{12}$ |
| Ad5Fib51 | $5.1 \times 10^{12}$ |

What is claimed is:

1. An in vitro method of delivering a nucleic acid of interest to a primary human chondrocyte, comprising:
   providing a recombinant adenovirus having a tropism for primary human chondrocytes, said recombinant adenovirus comprising:
      a nucleic acid of interest operatively linked to a promoter, wherein said nucleic acid of interest encodes at least one amino acid sequence that inhibits cartilage disease progression, at least one amino acid sequence that counteracts the loss of cartilage, or a combination thereof;
      a deletion in a gene encoding a fiber protein; and
      a nucleic acid replacing the deletion in the gene of the fiber protein, said nucleic acid encoding at least a part of a fiber protein of a B-type adenovirus, and wherein said at least a part of the fiber protein of the B-type adenovirus has a tropism for primary human chondrocytes; and
   infecting a primary human chondrocyte in vitro with said recombinant adenovirus, such that said nucleic acid of interest is delivered to said primary human chondrocyte.

2. The method of claim 1, wherein said B-type adenovirus is adenovirus type 35.

3. The method of claim 1, wherein said recombinant adenovirus comprises an adenovirus 5 nucleic acid sequence.

4. The method of claim 2, wherein said recombinant adenovirus comprises an adenovirus 5 genome.

5. The method of claim 1, wherein said recombinant adenovirus comprises at least one deletion in the E3 region where the nucleic acid of interest is inserted or can be inserted.

6. In vitro chondrocytes provided with an additional nucleic acid encoding:
   at least one amino acid sequence that inhibits cartilage disease progression;
   at least one amino acid sequence that counteracts the loss of cartilage; or
   a combination thereof;
   said additional nucleic acid provided by a gene delivery vehicle comprising a recombinant adenovirus having a tropism for chondrocytes;
   said recombinant adenovirus comprising:
      a deletion in a gene encoding a fiber protein; and
      a nucleic acid replacing the deletion in the gene encoding the fiber protein, said nucleic acid encoding at least a part of a fiber protein of a B-type adenovirus wherein said at least a part of the fiber protein of the B-type adenovirus has a tropism for primary human chondroctyes.

7. The in vitro chondrocytes of claim 6, wherein said additional nucleic acid encodes at least one member of the family of bone morphogenesis proteins.

8. An in vitro method of transducing a primary human chondrocyte, the method comprising:
   preparing a recombinant adenovirus having a tropism for primary human chondrocytes, said recombinant adenovirus including:
      a nucleic acid encoding a protein useful in inhibiting cartilage disease progression operatively linked to a promoter;
      a deletion in a gene encoding a fiber protein; and
      a nucleic acid replacing the deletion in the gene encoding the fiber protein, said nucleic acid encoding at least a part of a fiber protein of a B-type adenovirus, and wherein said at least a part of the fiber protein of the B-type adenovirus has a tropism for primary human chondrocytes; and
   infecting a primary human chondrocyte in vitro with said recombinant adenovirus, such that said nucleic acid of interest encoding the protein useful in inhibiting cartilage disease progression is expressed in said primary human chondrocyte.

9. An in vitro method of transducing a primary human chondrocyte, the method comprising:
   preparing a recombinant adenovirus having a tropism for primary human chondrocytes, said recombinant adenovirus including:
      a nucleic acid encoding a protein useful in repairing cartilage operatively linked to a promoter;
      a deletion in a gene encoding a fiber protein; and
      a nucleic acid replacing the deletion in the gene encoding the fiber protein, said nucleic acid encoding at least a part of a fiber protein of a B-type adenovirus, and wherein said at least a part of the fiber protein of the B-type adenovirus has a tropism for primary human chondrocytes; and
   infecting a primary human chondrocyte in vitro with said recombinant adenovirus, such that said nucleic acid encoding the protein useful in repairing cartilage is expressed in said primary human chondrocyte.

10. An in vitro method of delivering a nucleic acid of interest to a primary human chondrocyte, comprising:
   providing a recombinant adenovirus having a tropism for primary human chondrocytes, said recombinant adenovirus comprising:
      a nucleic acid of interest operatively linked to a promoter, wherein said nucleic acid of interest encodes at least one member of the family of bone morphogenesis proteins;
      a deletion in a gene encoding a fiber protein; and
      a nucleic acid replacing the deletion in the gene of the fiber protein, said nucleic acid encoding at least a part of the fiber protein of a B-type adenovirus, wherein said at least a part of the fiber protein of the B-type adenovirus has a tropism for primary human chondrocytes; and
   infecting a primary human chondrocyte in vitro with said recombinant adenovirus, such that said nucleic acid of interest is delivered to said primary human chondrocyte.

* * * * *

SEQUENCE LISTING

<160> NUMBER OF SEQ ID NOS: 14

<210> SEQ ID NO 1
<211> LENGTH: 23
<212> TYPE: DNA
<213> ORGANISM: unknown
<220> FEATURE:
<223> OTHER INFORMATION: Relating to Field of Human Gene Therapy

<400> SEQUENCE: 1
aattgtctta attaaccgct taa          23

```
<210> SEQ ID NO 2
<211> LENGTH: 19
<212> TYPE: DNA
<213> ORGANISM: unknown
<220> FEATURE:
<223> OTHER INFORMATION: Relating to Field of Human Gene Therapy

<400> SEQUENCE: 2
aattgtctta attaaccgc                                                     19

<210> SEQ ID NO 3
<211> LENGTH: 19
<212> TYPE: DNA
<213> ORGANISM: unknown
<220> FEATURE:
<223> OTHER INFORMATION: Relating to Field of Human Gene Therapy

<400> SEQUENCE: 3
aattgcggtt aattaagac                                                     19

<210> SEQ ID NO 4
<211> LENGTH: 47
<212> TYPE: DNA
<213> ORGANISM: unknown
<220> FEATURE:
<223> OTHER INFORMATION: Relating to Field of Human Gene Therapy

<400> SEQUENCE: 4
ctgtacgtac cagtgcactg gcctaggcat ggaaaaatac ataactg                      47

<210> SEQ ID NO 5
<211> LENGTH: 64
<212> TYPE: DNA
<213> ORGANISM: unknown
<220> FEATURE:
<223> OTHER INFORMATION: Relating to Field of Human Gene Therapy

<400> SEQUENCE: 5
gcggatcctt cgaaccatgg taagcttggt accgctagcg ttaaccgggc gactcagtca        60
atcg                                                                     64

<210> SEQ ID NO 6
<211> LENGTH: 28
<212> TYPE: DNA
<213> ORGANISM: unknown
<220> FEATURE:
<223> OTHER INFORMATION: Relating to Field of Human Gene Therapy

<400> SEQUENCE: 6
gcgccaccat gggcagagcg atggtggc                                           28

<210> SEQ ID NO 7
<211> LENGTH: 50
<212> TYPE: DNA
<213> ORGANISM: unknown
<220> FEATURE:
<223> OTHER INFORMATION: Relating to Field of Human Gene Therapy

<400> SEQUENCE: 7
gttagatcta agcttgtcga catcgatcta ctaacagtag agatgtagaa                   50

<210> SEQ ID NO 8
<211> LENGTH: 21
<212> TYPE: DNA
```

```
<213> ORGANISM: unknown
<220> FEATURE:
<223> OTHER INFORMATION: Relating to Field of Human Gene Therapy

<400> SEQUENCE: 8
gggtattagg ccaaaggcgc a                                        21

<210> SEQ ID NO 9
<211> LENGTH: 33
<212> TYPE: DNA
<213> ORGANISM: unknown
<220> FEATURE:
<223> OTHER INFORMATION: Relating to Field of Human Gene Therapy

<400> SEQUENCE: 9
gatcccatgg aagcttgggt ggcgacccca gcg                           33

<210> SEQ ID NO 10
<211> LENGTH: 36
<212> TYPE: DNA
<213> ORGANISM: unknown
<220> FEATURE:
<223> OTHER INFORMATION: Relating to Field of Human Gene Therapy

<400> SEQUENCE: 10
gatcccatgg ggatccttta ctaagttaca aagcta                        36

<210> SEQ ID NO 11
<211> LENGTH: 19
<212> TYPE: DNA
<213> ORGANISM: unknown
<220> FEATURE:
<223> OTHER INFORMATION: Relating to Field of Human Gene Therapy

<400> SEQUENCE: 11
gtcgctgtag ttggactgg                                           19

<210> SEQ ID NO 12
<211> LENGTH: 42
<212> TYPE: DNA
<213> ORGANISM: unknown
<220> FEATURE:
<223> OTHER INFORMATION: Relating to Field of Human Gene Therapy

<400> SEQUENCE: 12
cgacatatgt agatgcatta gtttgtgtta tgtttcaacg tg                 42

<210> SEQ ID NO 13
<211> LENGTH: 18
<212> TYPE: DNA
<213> ORGANISM: unknown
<220> FEATURE:
<223> OTHER INFORMATION: Relating to Field of Human Gene Therapy

<400> SEQUENCE: 13
ggagaccact gccatgtt                                            18

<210> SEQ ID NO 14
<211> LENGTH: 6
<212> TYPE: PRT
<213> ORGANISM: unknown
<220> FEATURE:
<223> OTHER INFORMATION: conserved tail region sequence of fiber protein

<400> SEQUENCE: 14
```

```
-continued

Phe Asn Pro Val Tyr Pro
1               5
```